(12) United States Patent
Narayan et al.

(10) Patent No.: US 10,271,744 B2
(45) Date of Patent: *Apr. 30, 2019

(54) SYSTEM AND METHOD TO IDENTIFY SOURCES ASSOCIATED WITH BIOLOGICAL RHYTHM DISORDERS

(71) Applicants: The Regents of the University of California, Oakland, CA (US); Topera, Inc., Menlo Park, CA (US)

(72) Inventors: Sanjiv Narayan, La Jolla, CA (US); Carey Robert Briggs, La Jolla, CA (US); Ruchir Sehra, Scottsdale, AZ (US)

(73) Assignees: The Regents of the University of California, Oakland, CA (US); The United States of America as Represented by the Department of Veterans Affairs, Washington, DC (US); Topera, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/136,268

(22) Filed: Apr. 22, 2016

(65) Prior Publication Data

US 2016/0235311 A1 Aug. 18, 2016

Related U.S. Application Data

(62) Division of application No. 13/844,562, filed on Mar. 15, 2013, now Pat. No. 9,332,915.

(51) Int. Cl.
*A61B 5/024* (2006.01)
*A61B 5/00* (2006.01)
(Continued)

(52) U.S. Cl.
CPC ........ *A61B 5/02405* (2013.01); *A61B 5/0002* (2013.01); *A61B 5/0006* (2013.01);
(Continued)

(58) Field of Classification Search
CPC ..................... A61B 5/02405; A61B 5/04525
See application file for complete search history.

(56) References Cited

U.S. PATENT DOCUMENTS 4,421,114 A 12/1983 Berkovits et al.
4,630,204 A 12/1986 Mortara
(Continued)

FOREIGN PATENT DOCUMENTS

CN 101461711 A 6/2009
EP 2269691 A2 1/2011
(Continued)

OTHER PUBLICATIONS

Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.
(Continued)

*Primary Examiner* — Carl H Layno
*Assistant Examiner* — Jennifer Ghand
(74) *Attorney, Agent, or Firm* — Scott Davison; Eleanor Musick; Musick Davison LLP

(57) ABSTRACT

In a system and method for identifying a driver of a source associated with a heart rhythm disorder, data are accessed from a plurality of sensors representing biological activity in the heart. A first region and a second region of the heart, which comprise the source of the heart rhythm disorder, are identified. If the first region of the heart has repeating centrifugal activation and controls the second region of the heart for at least a predetermined number of beats, the first
(Continued)

region is identified as controlling the source of the heart rhythm disorder.

32 Claims, 9 Drawing Sheets
(1 of 9 Drawing Sheet(s) Filed in Color)

(51) Int. Cl.
  *A61B 5/042* (2006.01)
  *A61B 5/04* (2006.01)
  *A61B 5/044* (2006.01)
  *A61B 5/0452* (2006.01)
  *A61B 5/046* (2006.01)

(52) U.S. Cl.
  CPC .......... *A61B 5/02444* (2013.01); *A61B 5/044* (2013.01); *A61B 5/046* (2013.01); *A61B 5/04012* (2013.01); *A61B 5/0422* (2013.01); *A61B 5/0452* (2013.01); *A61B 5/6852* (2013.01); *A61B 2560/0475* (2013.01); *A61B 2562/04* (2013.01)

(56) References Cited

U.S. PATENT DOCUMENTS

| | | |
|---|---|---|
| 4,754,763 A | 7/1988 | Doemland |
| 4,905,707 A | 3/1990 | Davies et al. |
| 4,905,708 A | 3/1990 | Davies |
| 5,029,082 A | 7/1991 | Shen et al. |
| 5,092,341 A | 3/1992 | Kelen |
| 5,121,750 A | 6/1992 | Katims |
| 5,172,699 A | 12/1992 | Svenson et al. |
| 5,178,154 A | 1/1993 | Ackmann et al. |
| 5,366,487 A | 11/1994 | Adams et al. |
| 5,427,112 A | 6/1995 | Noren et al. |
| 5,433,198 A | 7/1995 | Desai |
| 5,439,483 A | 8/1995 | Duong-Van |
| 5,450,846 A | 9/1995 | Goldreyer |
| 5,458,621 A | 10/1995 | White et al. |
| 5,480,422 A | 1/1996 | Ben-Haim |
| 5,487,391 A | 1/1996 | Panescu |
| 5,582,173 A | 12/1996 | Li |
| 5,645,070 A | 7/1997 | Turcott |
| 5,657,755 A | 8/1997 | Desai |
| 5,662,108 A | 9/1997 | Budd et al. |
| 5,687,737 A | 11/1997 | Branham et al. |
| 5,718,241 A | 2/1998 | Ben-Haim et al. |
| 5,795,303 A | 8/1998 | Swanson et al. |
| 5,810,740 A | 9/1998 | Paisner |
| 5,817,134 A | 10/1998 | Greenhut et al. |
| 5,819,740 A | 10/1998 | Muhlenberg |
| 5,836,889 A | 11/1998 | Wyborny et al. |
| 5,840,025 A | 11/1998 | Ben-Haim |
| 5,848,972 A | 12/1998 | Triedman et al. |
| 5,868,680 A | 2/1999 | Steiner et al. |
| 5,954,661 A | 9/1999 | Greenspon et al. |
| 5,954,665 A | 9/1999 | Ben-Haim |
| 6,052,618 A | 4/2000 | Dahlke et al. |
| 6,066,094 A | 5/2000 | Ben-Haim |
| 6,097,983 A | 8/2000 | Strandberg |
| 6,112,117 A | 8/2000 | Kenknight et al. |
| 6,115,628 A | 9/2000 | Stadler et al. |
| 6,188,924 B1 | 2/2001 | Swanson et al. |
| 6,208,888 B1 | 3/2001 | Yonce |
| 6,236,883 B1 | 5/2001 | Ciaccio et al. |
| 6,251,125 B1 | 6/2001 | Kenknight et al. |
| 6,256,540 B1 | 7/2001 | Panescu et al. |
| 6,301,496 B1 | 10/2001 | Reisfeld |
| 6,324,421 B1 | 11/2001 | Stadler et al. |
| 6,360,121 B1 | 3/2002 | Shoda et al. |
| 6,397,100 B2 | 5/2002 | Stadler et al. |
| 6,438,406 B2 | 8/2002 | Yonce |
| 6,438,409 B1 | 8/2002 | Malik et al. |
| 6,449,503 B1 | 9/2002 | Hsu |
| 6,510,339 B2 | 1/2003 | Kovtun et al. |
| 6,522,905 B2 | 2/2003 | Desai |
| 6,539,256 B1 | 3/2003 | Kenknight et al. |
| 6,542,773 B2 | 4/2003 | Dupree et al. |
| 6,553,251 B1 | 4/2003 | Lähdesmäki |
| 6,584,345 B2 | 6/2003 | Govari |
| 6,725,085 B2 | 4/2004 | Schwartzman et al. |
| 6,738,655 B1 | 5/2004 | Sen et al. |
| 6,788,969 B2 | 9/2004 | Dupree et al. |
| 6,847,839 B2 | 1/2005 | Ciaccio et al. |
| 6,856,830 B2 | 2/2005 | He |
| 6,889,081 B2 | 5/2005 | Hsu |
| 6,892,091 B1 | 5/2005 | Ben-Haim et al. |
| 6,920,350 B2 | 7/2005 | Xue et al. |
| 6,941,166 B2 | 9/2005 | MacAdam et al. |
| 6,950,696 B2 | 9/2005 | Bjorling et al. |
| 6,950,702 B2 | 9/2005 | Sweeney |
| 6,959,212 B2 | 10/2005 | Hsu et al. |
| 6,975,900 B2 | 12/2005 | Rudy et al. |
| 6,978,168 B2 | 12/2005 | Beatty et al. |
| 6,985,768 B2 | 1/2006 | Hemming et al. |
| 7,016,719 B2 | 3/2006 | Rudy et al. |
| 7,043,292 B2 | 5/2006 | Tarjan et al. |
| 7,076,288 B2 | 7/2006 | Skinner |
| 7,117,030 B2 | 10/2006 | Berenfeld et al. |
| 7,123,954 B2 | 10/2006 | Narayan et al. |
| 7,206,630 B1 | 4/2007 | Tarler |
| 7,215,993 B2 | 5/2007 | Lin |
| 7,245,962 B2 | 7/2007 | Ciaccio et al. |
| 7,263,397 B2 | 8/2007 | Hauck et al. |
| 7,283,865 B2 | 10/2007 | Noren |
| 7,289,843 B2 | 10/2007 | Beatty et al. |
| 7,289,845 B2 | 10/2007 | Sweeney et al. |
| 7,328,063 B2 | 2/2008 | Zhang et al. |
| 7,369,890 B2 | 5/2008 | Lovett |
| 7,457,664 B2 | 11/2008 | Zhang et al. |
| 7,505,810 B2 | 3/2009 | Harlev et al. |
| 7,509,170 B2 | 3/2009 | Zhang et al. |
| 7,515,954 B2 | 4/2009 | Harlev et al. |
| 7,567,835 B2 | 7/2009 | Gunderson et al. |
| 7,580,744 B2 | 8/2009 | Hsu |
| 7,620,446 B2 | 11/2009 | Ferek-Petric |
| 7,657,307 B2 | 2/2010 | Dam et al. |
| 7,729,753 B2 | 6/2010 | Kremliovsky et al. |
| 7,734,333 B2 | 6/2010 | Ghanem et al. |
| 7,734,336 B2 | 6/2010 | Ghanem et al. |
| 7,738,948 B2 | 6/2010 | Rouw et al. |
| 7,742,812 B2 | 6/2010 | Ghanem et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,801,594 B1 | 9/2010 | Higham |
| 7,907,993 B2 | 3/2011 | Ghanem et al. |
| 7,907,994 B2 | 3/2011 | Stolarski et al. |
| 7,930,018 B2 | 4/2011 | Harlev et al. |
| 7,930,020 B2 | 4/2011 | Zhang et al. |
| 7,953,475 B2 | 5/2011 | Harlev et al. |
| 7,962,202 B2 | 6/2011 | Bhunia |
| 8,050,732 B2 | 11/2011 | Desai |
| 8,050,751 B2 | 11/2011 | Zhang et al. |
| 8,050,757 B2 | 11/2011 | Hsu |
| 8,095,205 B2 | 1/2012 | Bhunia |
| 8,095,206 B2 | 1/2012 | Ghanem et al. |
| 8,160,684 B2 | 4/2012 | Ghanem et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,306,618 B2 | 11/2012 | Ghanem et al. |
| 8,315,697 B2 | 11/2012 | Hsu |
| 8,340,766 B2 | 12/2012 | Ryu et al. |
| 8,386,024 B2 | 2/2013 | Gunderson et al. |
| 8,435,185 B2 | 5/2013 | Ghanem et al. |
| 8,489,171 B2 | 7/2013 | Hauck et al. |
| 8,521,266 B2 | 8/2013 | Narayan et al. |
| 8,588,885 B2 | 11/2013 | Hall et al. |
| 8,594,777 B2 | 11/2013 | Briggs et al. |
| 8,639,325 B2 | 1/2014 | Efimov et al. |

(56) References Cited

U.S. PATENT DOCUMENTS

| | | | |
|---|---|---|---|
| 8,676,303 B2 | 3/2014 | Narayan | |
| 8,700,140 B2 | 4/2014 | Narayan et al. | |
| 8,715,199 B1 | 5/2014 | Macneil et al. | |
| 8,812,074 B2 | 8/2014 | Kordis et al. | |
| 8,838,222 B2 | 9/2014 | Narayan et al. | |
| 8,838,223 B2 | 9/2014 | Narayan et al. | |
| 8,868,169 B2 | 10/2014 | Narayan et al. | |
| 9,031,642 B2 | 5/2015 | Ghosh | |
| 9,050,006 B2 | 6/2015 | Narayan et al. | |
| 9,055,876 B2 | 6/2015 | Narayan et al. | |
| 9,055,877 B2 | 6/2015 | Narayan et al. | |
| 9,055,878 B2 | 6/2015 | Narayan et al. | |
| 9,089,269 B2 | 7/2015 | Narayan et al. | |
| 9,107,600 B2 | 8/2015 | Narayan et al. | |
| 9,220,427 B2 | 12/2015 | Narayan et al. | |
| 9,241,667 B2 | 1/2016 | Narayan et al. | |
| 9,282,910 B2 | 3/2016 | Narayan et al. | |
| 9,332,915 B2* | 5/2016 | Narayan | A61B 5/0006 |
| 9,375,156 B2 | 6/2016 | Narayan et al. | |
| 9,380,950 B2 | 7/2016 | Narayan et al. | |
| 9,392,948 B2 | 7/2016 | Briggs et al. | |
| 9,393,425 B2 | 7/2016 | Narayan | |
| 9,398,860 B2 | 7/2016 | Macneil et al. | |
| 9,398,883 B2 | 7/2016 | Narayan et al. | |
| 9,408,536 B2 | 8/2016 | Narayan et al. | |
| 9,439,573 B2 | 9/2016 | Narayan et al. | |
| 9,468,387 B2 | 10/2016 | Narayan et al. | |
| 9,549,684 B2 | 1/2017 | Narayan et al. | |
| 9,668,666 B2 | 6/2017 | Narayan et al. | |
| 9,955,879 B2 | 5/2018 | Narayan et al. | |
| 2003/0018277 A1 | 1/2003 | He | |
| 2003/0083587 A1 | 5/2003 | Ferek-Petric | |
| 2004/0093035 A1 | 5/2004 | Schwartz et al. | |
| 2004/0243014 A1 | 12/2004 | Lee et al. | |
| 2005/0137638 A1 | 6/2005 | Yonce et al. | |
| 2005/0203502 A1 | 9/2005 | Boveja et al. | |
| 2006/0161069 A1 | 7/2006 | Li | |
| 2007/0016261 A1 | 1/2007 | Dong et al. | |
| 2007/0055167 A1 | 3/2007 | Bullinga | |
| 2007/0208260 A1 | 9/2007 | Afonso | |
| 2007/0208263 A1 | 9/2007 | John et al. | |
| 2007/0232948 A1 | 10/2007 | Stadler et al. | |
| 2007/0299351 A1 | 12/2007 | Harlev et al. | |
| 2008/0097539 A1 | 4/2008 | Belalcazar | |
| 2008/0109041 A1 | 5/2008 | de Voir | |
| 2008/0114258 A1 | 5/2008 | Zhang et al. | |
| 2008/0208012 A1 | 8/2008 | Ali | |
| 2008/0319332 A1 | 12/2008 | Sornmo et al. | |
| 2009/0069704 A1 | 3/2009 | MacAdam et al. | |
| 2009/0099468 A1 | 4/2009 | Thiagalingam et al. | |
| 2009/0099618 A1 | 4/2009 | Rousso et al. | |
| 2009/0112106 A1 | 4/2009 | Zhang | |
| 2009/0112110 A1 | 4/2009 | Zhang | |
| 2009/0112199 A1 | 4/2009 | Zhang et al. | |
| 2009/0131760 A1 | 5/2009 | Ali et al. | |
| 2009/0163968 A1 | 6/2009 | Donofrio | |
| 2009/0259266 A1 | 10/2009 | Zhang et al. | |
| 2009/0299203 A1 | 12/2009 | de Voir et al. | |
| 2010/0026543 A1 | 2/2010 | Tsai et al. | |
| 2010/0204592 A1 | 8/2010 | Hatib et al. | |
| 2010/0217143 A1 | 8/2010 | Whittington et al. | |
| 2010/0249627 A1 | 9/2010 | Zhang et al. | |
| 2010/0298729 A1 | 11/2010 | Zhang et al. | |
| 2010/0305456 A1 | 12/2010 | Brainard, II | |
| 2010/0324435 A1 | 12/2010 | Higham | |
| 2011/0077540 A1 | 3/2011 | Belalcazar | |
| 2011/0087121 A1 | 4/2011 | Zhang et al. | |
| 2011/0112425 A1 | 5/2011 | Muhlsteff et al. | |
| 2011/0118803 A1 | 5/2011 | Hou et al. | |
| 2011/0130801 A1 | 6/2011 | Maskara et al. | |
| 2011/0196249 A1 | 8/2011 | Staeuber et al. | |
| 2011/0257547 A1 | 10/2011 | Zhang | |
| 2011/0282227 A1 | 11/2011 | Zhang | |
| 2012/0184858 A1 | 7/2012 | Harlev et al. | |
| 2012/0184863 A1 | 7/2012 | Harlev et al. | |
| 2012/0232417 A1 | 9/2012 | Zhang | |
| 2013/0006131 A1* | 1/2013 | Narayan | A61B 5/042 600/508 |
| 2013/0245474 A1 | 9/2013 | Nicolson et al. | |
| 2013/0324871 A1 | 12/2013 | Dubois et al. | |
| 2013/0345577 A1 | 12/2013 | Thakur et al. | |
| 2014/0005562 A1 | 1/2014 | Bunch et al. | |
| 2014/0235988 A1 | 8/2014 | Ghosh | |
| 2014/0276152 A1 | 9/2014 | Narayan et al. | |
| 2014/0336520 A1 | 11/2014 | Zeng et al. | |
| 2014/0371609 A1 | 12/2014 | Narayan et al. | |
| 2014/0371613 A1 | 12/2014 | Narayan et al. | |
| 2014/0371616 A1 | 12/2014 | Narayan et al. | |
| 2015/0038861 A1 | 2/2015 | Narayan et al. | |
| 2015/0257710 A1 | 9/2015 | Narayan et al. | |
| 2015/0366476 A1 | 12/2015 | Laughner et al. | |
| 2016/0015283 A1 | 1/2016 | Narayan et al. | |
| 2016/0022163 A1 | 1/2016 | Narayan et al. | |
| 2016/0095531 A1 | 4/2016 | Narayan et al. | |
| 2016/0166167 A1 | 6/2016 | Narayan et al. | |
| 2016/0262643 A1 | 9/2016 | Ng et al. | |
| 2016/0302734 A1 | 10/2016 | Narayan | |
| 2016/0360983 A1 | 12/2016 | Narayan et al. | |
| 2016/0374571 A1 | 12/2016 | Narayan et al. | |
| 2017/0007176 A1 | 1/2017 | Narayan et al. | |
| 2017/0049402 A1 | 2/2017 | Narayan et al. | |
| 2017/0311835 A1 | 11/2017 | Narayan et al. | |
| 2017/0340229 A1 | 11/2017 | Narayan et al. | |

FOREIGN PATENT DOCUMENTS

| | | | |
|---|---|---|---|
| EP | 1808124 B1 | 4/2011 | |
| EP | 2638854 A1 | 9/2013 | |
| JP | H05502816 A | 5/1993 | |
| JP | H09215667 A | 8/1997 | |
| WO | 1991019452 A1 | 12/1991 | |
| WO | 1994021168 A1 | 9/1994 | |
| WO | 1996025096 A1 | 8/1996 | |
| WO | 2005035046 A2 | 4/2005 | |
| WO | 2005115232 A1 | 12/2005 | |
| WO | 2006066324 A1 | 6/2006 | |
| WO | 2007078421 A2 | 7/2007 | |
| WO | 2007106829 A2 | 9/2007 | |
| WO | 2007146864 A2 | 12/2007 | |
| WO | 2008035070 A2 | 3/2008 | |
| WO | 2013150740 A1 | 10/2013 | |

OTHER PUBLICATIONS

Eckman, et al., "Recurrence plots of dynamical systems," Europhys. Lett., 4 (3), Nov. 1, 1987 pp. 973-977.

EP 09819953 Supplementary European Search Report & European Search Opinion dated Feb. 7, 2012, 12 pages.

EP 12711553 Supplementary European Search Report & European Search Opinion , dated Sep. 11, 2013, 7 pages.

EP 12779506.0 Supplementary European Search Report & European Search Opinion dated Nov. 18, 2014, 8 pages.

EP 12855266.8: Supplementary European Search Report & European Search Opinion, dated Jun. 2, 2015, 9 pages.

EP 12855738.6: Supplementary European Search Report & European Search Opinion, dated Jun. 5, 2015, 9 pages.

EP 15192804.1 Supplementary European Search Report, dated Feb. 18, 2016, 7 pages.

Holm, M. et al., "A New Method for Analysis of Atrial Activation During Chronic Atrial Fibrillation in Man", IEEE Transactions on Biomedical Engineering, vol. 43, No. 2, Feb. 1, 1996, pp. 198-210.

Houben, R.P.M., et al, "Automatic mapping of human atrial fibrillation by template matching", Heart Rhythm, vol. 3, No. 10, Oct. 1, 2006, pp. 1221-1228.

Houben, R.P.M., et al., "Processing of Intracardiac Electrograms in Atrial Fibrillation", IEEE Engineering in Medicine and Biology Magazine, Nov./Dec. 2006, pp. 40-51.

Kadish, A., et al., "Characterization of fibrillatory rhythms by ensemble vector directional analysis", Am J Physiol.—Heart Circ. Physiol., vol. 285, Oct. 2003, pp. H1705-H1719.

(56) References Cited

OTHER PUBLICATIONS

Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.
Masse, S., et al., "Wave similarity of human ventricular fibrillation from bipolar electrograms",Eurospace (2007) vol. 9, pp. 10-19.
Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.
Narayan, S.M., et al., "Dynamics factors preceding the initiation of atrial fibrillation in humans", Heart Rhythm, vol. 5, No. 6, Jun. 1, 2008, pp. S22-S25.
PCT/US/2014/029645 International Search Report and Written Opinion, dated Aug. 18, 2014, 17 pages.
PCT/US/2015/023929: International Search Report and Written Opinion, dated Jul. 9, 2015, 8 pages.
PCT/US2009/060178 International Preliminary Report on Patentability and Written Opinion, dated Apr. 12, 2011, 10 pages.
PCT/US2011/031468 International Preliminary Report on Patentability and Written Opinion, dated Oct. 9, 2012, 8 pages.
PCT/US2011/031470 International Preliminary Report on Patentability and Written Opinion, dated Oct. 9, 2012, 7 pages.
PCT/US2012/029935 International Search Report and Written Opinion, dated Nov. 8, 2012, 9 pages.
PCT/US2012/036157 International Preliminary Report on Patentability and Written Opinion, dated Aug. 14, 2012, 8 pages.
PCT/US2012/068639 International Preliminary Report on Patentability and Written Opinion, dated Jun. 10, 2013; 6 pages.
PCT/US2012/068640 International Preliminary Report on Patentability and Written Opinion, dated Jun. 10, 2013; 5 pages.
PCT/US2014/029616 International Search Report and Written Opinion, dated Sep. 18, 2014; 9 pages.
PCT/US2015/046742 International Search Report and Written Opinion; dated Dec. 1, 2015, 5 pages.
Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.
Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.
Sun, Yan, et al., "Characteristic wave detection in ECG signal using morphological transform", BMC Cardiovascular Disorders, vol. 5, No. 28, 2005.
Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.
Ulphani, J.S., et al., "Frequency gradients during two different forms of fibrillation in canine atria", Heart Rhythm, vol. 4, No. 10, Oct. 2007, pp. 1315-1323.
Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 238-335.
Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.
English-language translation of Chinese patent publication No. CN 101461711A, published Jun. 24, 2009.
EP14763969.4 Supplementary European Search Report & European Search Opinion dated Oct. 21, 2016, 7 pages.
EP147665096.4 Supplementary European Search Report & European Search Opinion, dated Oct. 21, 2016, 6 pages.
Jung, TP et al, Removing Electroencephalographic Artifacts by Blind Source Separation, Psychophysiology, 37.02 (2000): 163-178.
Botteron, G.W. et al., A technique for measurement of the extent of spatial organization of atrial activation during atrial fibrillation in the intact human heart, IEEE Transactions on Biomedical Engineering, Jun. 1995, pp. 579-586, vol. 42, No. 6.
Censi, F. et al., "Recurrent Patterns of Atrial Depolarization During Atrial Fibrillation Assessed by Recurrence Plot Quantification", Annals of Biomedical Engineering, 2000, pp. 61-70; vol. 28.
EP15774130.7 Supplementary European Search Report & European Search Opinion, dated Nov. 15, 2017, 9 pages.
EP15836641 Supplementary European Search Report & European Search Opinion, dated Mar. 8, 2018, 8 pages.
PCT/US2017/030683, International Search Report and Written Opinion, dated Aug. 1, 2017, 6 pages.
Xiao, Yuping et al., Parameter estimation of spiral waves from atrial electrograms:, Proceedings of International Conference on Acoustics, Speech and Signal Processing (ICASSP '03) Apr. 6-10, 2003, Hong Kong, China, IEEE, 2003 IEEE International Conference, vol. 5, Apr. 6, 2003, pp. V_245-V_248.

* cited by examiner

SYSTEM AND METHOD TO IDENTIFY SOURCES ASSOCIATED WITH BIOLOGICAL RHYTHM DISORDERS

CROSS REFERENCE TO RELATED APPLICATIONS

This application is a divisional of U.S. patent application Ser. No. 13/844,562, filed on Mar. 15, 2013, issued as U.S. Pat. No. 9,332,915, which is incorporated herein by reference in its entirety.

GOVERNMENT RIGHTS

This invention was made with government support under Grants R01 HL83359 and HL 103800 from the National Institutes of Health. The government has certain rights in the invention.

BACKGROUND

Field of the Disclosure

The present application relates generally to biological rhythm disorders. More specifically, the present application is directed to a system and method to define drivers of sources associated with biological rhythm disorders, such as heart rhythm disorders.

Brief Discussion of Related Art

Heart (cardiac) rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders, which are more simple to treat, but which may also be clinically significant, include atrial tachycardia (AT), supraventricular tachycardia (SVT), atrial flutter (AFL), supraventricular ectopic complexes/beats (SVE) and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Previously, treatment of heart rhythm disorders—particularly complex rhythm disorders of AF, VF and polymorphic VT—has been difficult because the location in the heart that harbors the source of the heart rhythm disorder could not be identified. There have been various theories of how complex rhythm disorders function and clinical applications for treating these complex rhythm disorders. However, none of the applications proved fruitful in the treatment of complex rhythm disorders.

Recently, there has been a breakthrough discovery that for the first time identified sources associated with complex heart rhythm disorders. This technological breakthrough successfully reconstructed cardiac activation information (onset times) in signals obtained from electrodes of catheters introduced into patients' heart to identify rotational activation patterns (rotational sources) or centrifugal patterns (focal sources) that cause a large percentage of the heart rhythm disorders worldwide. Treatment of the heart rhythm disorders can thus be targeted to these rotational or focal sources in the patient's heart to eliminate the heart rhythm disorders. Such treatment can be successfully delivered by ablation, for example.

While a rotational or focal source of a complex heart rhythm disorder can be identified as described above, the inner mechanism of the source, i.e., the core of the rotational source (its likely center of rotation), or origin of a focal source, is not well defined. In some instances, a rotational source may have one or more diffuse sections (activation wave fronts) that generally appear to rotate around a subjective rotation center, but tend to spread out diffusely about a section of the patient's heart. While the diffuse activation wave fronts are associated with the source of the complex rhythm disorder, they may contribute insignificantly to driving the heart rhythm disorder than one or more other activation wave fronts of the rotational source. Similarly, the core of a centrifugally emanating focal source of a complex rhythm disorder has not been well defined.

It has thus far been undefined how to identify the core of a rotational source in contrast to an insignificant 'passive' rotation that is not a source of the heart rhythm disorder, or how to identify the origin of a true focal source in contrast to an occasional focal activation that can be secondary to a complex rhythm disorder, rather than its source.

There are no known systems or methods to define the core of a rotational source or the origin of a focal source associated with a heart rhythm disorder.

SUMMARY

In one aspect, a method of identifying a driver of a source associated with a heart rhythm disorder is disclosed. Data is accessed from a plurality of sensors representing biological activity in the heart. A local first region of the heart that has repeating activation and that controls a second distant region of the heart for at least a predetermined number of beats is identified. The first local region is assigned as a driver of a source of the heart rhythm disorder, the source including the first local region and the second distant region.

In another aspect, a system of identifying a driver of a source associated with a heart rhythm disorder is disclosed. The system includes a processor and a storage medium storing instructions that, when executed by the processor, cause the processor to perform certain operations. The operations include accessing data from a plurality of sensors representing biological activity in the heart. The operations also include identifying a local first region of the heart that has repeating activation and that controls a second distant region of the heart for at least a predetermined number of beats. The operations further include assigning the first local region as a driver of a source of the heart rhythm disorder, the source including the first local region and the second distant region.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments or aspects are illustrated by way of example and not limitation in the figures of the accompanying drawings in which.

DETAILED DESCRIPTION

Figure 1:
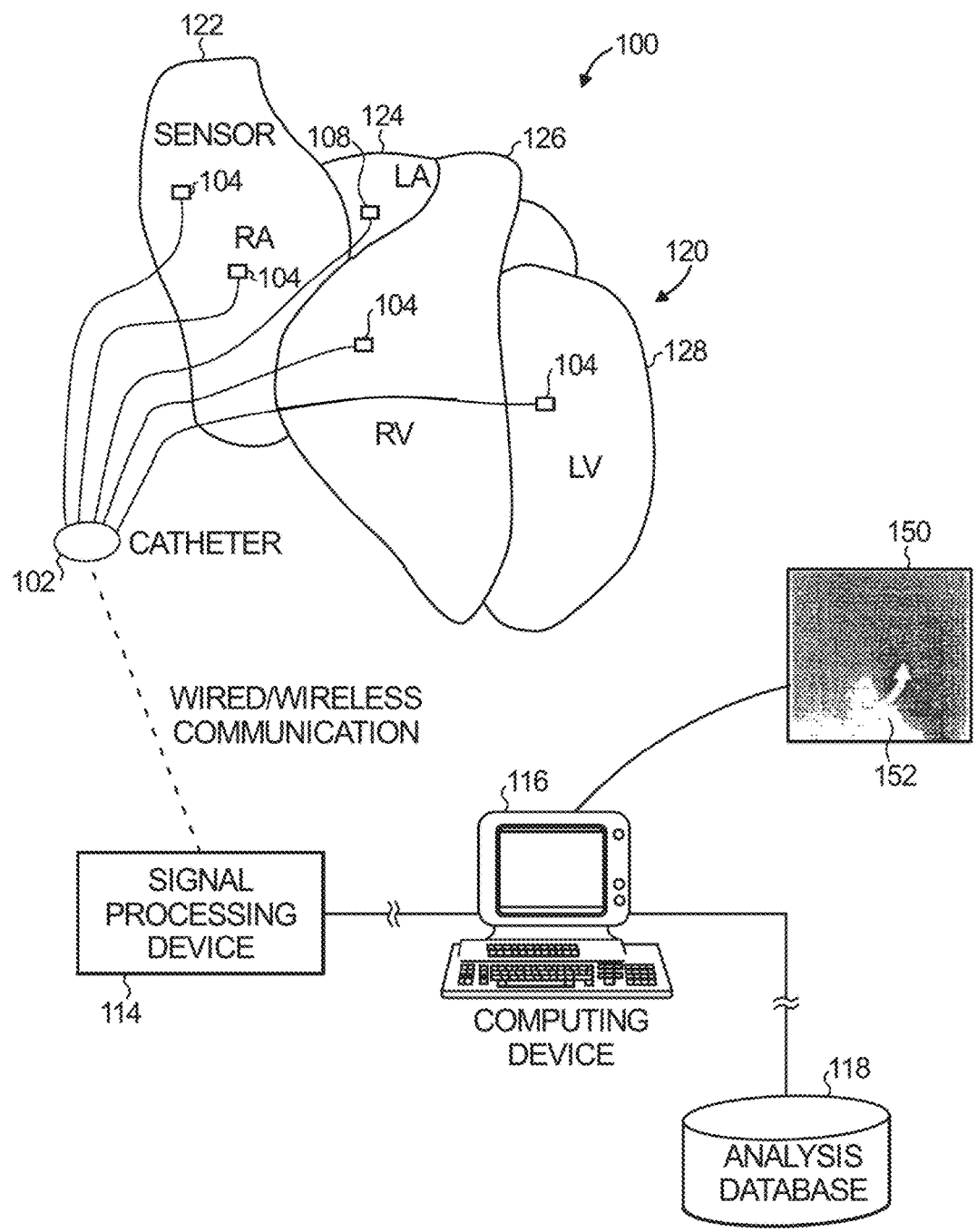
FIG. 1 illustrates a system to identify rotational patterns or centrifugal patterns indicating activation emanation from localized sources for heart rhythm disorders.

A system and method for defining drivers of sources associated with heart rhythm disorders are disclosed herein. In the following description, for the purposes of explanation, numerous specific details are set forth in order to provide a thorough understanding of example embodiments or aspects. It will be evident, however, to one skilled in the art, that an example embodiment may be practiced without all of the disclosed specific details.

The present disclosure is applicable to defining various drivers of sources associated with heart rhythm disorders. Drivers may be represented by persistent rotational activation around a center that may show movement ('meander' or 'precession'), or persistently repetitive activation from an origin. The disclosure can also be applied to other biological rhythm disorders, such as neurological seizures, esophageal spasms, bladder instability, irritable bowel syndrome, and other biological disorders for which biological activation information can be reconstructed to permit determination, diagnosis, and/or treatment of the cause or source of the disorders. It is particularly useful, however, in complex rhythm disorders which result in complex activation patterns, and especially useful in complex rhythm disorders of the heart such as atrial fibrillation, ventricular fibrillation and others, in order to find the driver(s) associated with source(s) of the complex rhythm disorders such that they can be treated with expediency.

Complex heart rhythm disorders, including but not limited to atrial fibrillation, polymorphic atrial tachycardia, ventricular fibrillation, polymorphic ventricular tachycardia and others, typically result in activation patterns that are extremely difficult to decipher.

A novel concept is that activation from a localized region of the heart must activate surrounding tissue during the heart rhythm disorder by definition, even for complex heart rhythm disorders. This control may proceed via a centrifugal activation from the local region to surrounding tissue, or by rotational (rotor) activation from the local region to surrounding tissue. The localized region (driver) for complex rhythm disorders generally occupies an area. This disclosure describes for the first time that the driver within a localized region may demonstrate activation sequences that are rotational or centrifugal, which may affect or control a remote region of the heart.

Thus, to identify or define the local region of a complex heart rhythm disorder, it is essential not just to identify its rotational or centrifugal driver, but it is also necessary to ensure that the driver controls activation in a distant region of the heart. These criteria can, therefore, help to eliminate many spurious or unimportant 'spins' or 'focal discharges' uncovered in the current state of the art that are not drivers of the sources associated with heart rhythm disorders, and can help to improve treatment where localized therapy has not been successful in the past.

The ability to determine accurate activation information of heart beats in complex disorders has previously been very difficult, such that targeted therapy aimed at the source(s) of these disorders has not been possible. Among the advantages of the present disclosure is the ability to recognize rotational electrical patterns, even amidst the virtually indiscernible sensed activation patterns, such that a determination of the source of the disorder can be determined and treated.

Complex rhythm disorders are directly caused by localized sources, from whence activation may take the form of spiral waves with rotational electrical activity, focal sources in which activation emanates centrifugally or a combination. The complexity of multiple concurrent drivers can cause disorganized activation patterns (sources), which have obscured prior attempts to map these rhythms. In this way, passive activation from colliding or secondary wave fronts may transiently obscure the detection of the source of the disorder, but not terminate its internal driver. In electrophysiological terms, this is similar to pacing 'entrainment' transiently altering activation sequences around a driver (e.g., in the Wolff-Parkinson-White syndrome or atrial flutter), with redetection of the driver when entrainment stops. The present disclosure shows that this is also true for detection of drivers of sources associated with complex rhythm disorders.

Accordingly, rotational electrical activity from a spiral wave (rotor, reentrant circuit) may appear to be insignificant, either in the degree or duration of the rotation, or have inconsistent rotation patterns. It has previously been unclear how to separate sources from transient activation of an occasional rotation or single cycle where activation appears to emanate from an origin, inherent in all complex rhythms. This task has been more difficult since sources for complex rhythms are not points, but occupy limited spatial areas within which the driver may move (termed "meander" or "precession")—akin to the movement of a spinning object in a gravity well.

The present disclosure provides a system and method for defining or identifying persistent rotational drivers or focal drivers within localized sources associated with complex rhythm disorders. Rotational drivers can be defined or identified by showing that activation sequences trace successive angles, or show successive angular sectors over time, or using phase mapping, vector analysis and other methods. Focal drivers can be identified by vectors, coherence, correlation, phase and other analytic methods to identify centrifugal activation from an origin. Additionally, the system and method of the present disclosure provide qualitative and/or quantitative indicators to indicate the strength, consistency, and duration of identified phase singularities.

Another advantage is that the present disclosure provides a system and method that can be carried out rapidly while a sensing device, e.g., a catheter having sensors thereon, is used in or near the patient and can be followed by treatment of cardiac tissue to ameliorate the disorder and in many cases cure the disorder. Treatment may thus occur immediately upon computing the rotational electrical pattern information of the driver of the source, since it will indicate the location(s) of the cause or source of the disorder.

FIG. 1 illustrates an example system for identifying the driver (an area of the heart) associated with the source of a heart rhythm disorder 100. The example system 100 is configured to identify a driver, in the form of persistent rotational or centrifugal patterns, associated with sensed cardiac electrical activity of a patient's heart 120 in connection with determining the source of a heart rhythm disorder. The heart 120 includes a right atrium 122, left atrium 124, right ventricle 126 and left ventricle 128.

The example system 100 includes a catheter 102, signal processing device 114, computing device 116 and analysis database 118. The catheter 102 is configured to detect cardiac electrical information in the heart and to transmit the detected cardiac electrical information to the signal processing device 114, either via a wireless or wired connection. The catheter includes an array of probes/sensors 104, which can be inserted into the heart through the patient's blood vessels. Sensors 104 may provide unipolar and/or bipolar signals.

In some aspects, one or more of the sensors 104 are not inserted into the patient's heart 120. For example, some sensors may detect cardiac electrical information via the patient's surface (e.g., electrocardiogram) or remotely without contact with the patient (e.g., magnetocardiogram or methods to identify electrical information via the inverse solution). As another example, some sensors may also derive cardiac electrical information from cardiac motion of a non-electrical sensing device (e.g., echocardiogram). In various embodiments or aspects, these sensors can be used separately or in different combinations, and further these separate or different combinations can also be used in combination with sensors inserted into the patient's heart 120.

The sensors 104 are positioned at respective sensor locations adjacent to or contacting tissue in the heart 120 or near the heart 120. The sensors 104 can detect cardiac electrical activity at the sensor locations and can generate corresponding sensing signals which are output to the signal processing device 114. The sensors 104 may further be configured to deliver energy to ablate the heart 120 at the sensor locations, particularly when the sensor location is adjacent to or contacting heart tissue.

The signal processing device 114 is configured to process (e.g., clarify and amplify) the sensing signals generated by the sensors 104 and to output corresponding cardiac signals. The computing device 116 receives (which refers to receiving or accessing) the cardiac signals and processes them in accordance with methods disclosed herein to identify rotational electrical activity (clockwise or counterclockwise) or centrifugal activity (indicating a focal driver) from the cardiac signals. Additionally, the computing device 116 identifies indices of driver activity that are persistent.

The computing device 116 displays an activation propagation map (APM) video 150 that combines and spatially lays out data from a plurality of monophasic action potential (MAP) voltage representations of the cardiac signals. The APM video 150 includes a sequence of APM frames that are associated with a series of time increments over a time interval. Arrow 152 indicates rotational movement of displayed information. Each element in the MAP representation is associated with a respective sensor 104 of the array of sensors. A MAP representation includes voltage (or charge) versus time and other indexes. For rotational drivers, detection may also use information on rotational angles, solid angles, angular velocity, and tangential velocity at the circumference of rotation and phase information. For focal sources, information may also include centrifugal indexes (such as velocity and acceleration), and centripetal indexes (such as velocity and acceleration). Centripetal indexes typically indicate a passive area (not a source), but may indicate a source that is moving away from the sensor. For all sources, quantification includes stigmata of dynamic movement such as Doppler shift, disorganization in the core, and measures of entropy since the driver may move constantly and dynamically within the source region. Information may also include activation onset time information associated with the electrical activity sensed by a sensor 104 of the array of sensors. The MAP representation can be mapped as curves on time and voltage axes, as well as several other representations including polar plots and three-dimensional plots.

As used herein, activation onset time is a time point at which activation commences in a cell or tissue, as opposed to other time points during activation. Activation is a process whereby a cell commences its operation from a quiescent (diastolic) state to an active (electrical) state.

The computing device 116 receives, accesses, or generates the signal representations and APM video 150. An example of generation of an APM video 150 and a signal representation in the form of a monophasic action potential (MAP) is described in U.S. Pat. No. 8,165,666, which is incorporated herein by reference in its entirety. In particular, FIG. 11 of the '666 patent illustrates an APM video 150 of MAPs. Other signals of value include noise-free unipolar electrograms and processed unipolar electrograms. Similarly, other systems and methods can reconstruct cardiac or biological activation information to include activation times, phase information and onset.

The APM video 150 may be generated by systems and methods that can display process or reconstruct cardiac or biological electrical information over time to generate a dynamic video representation of activation information, electrical activity, rotational activity and/or a core associated with the rotational activity, focal activity and/or the origin from where centrifugal activation emanates.

In one embodiment or aspect, rotational activation is indicated from phase mapping by a phase singularity, in which the dynamic activation information may exhibit rotational motion. The APM video 150 in this case may also display an indicator of a phase singularity, such as a white dot, that may be determined by calculations performed per frame. Each frame displays information based on measurements made at the time of the frame. The degree of confidence in each rotational driver in this embodiment is indicated by the persistence of a phase singularity over time. Singularities detected for only a short amount of time may displayed in only a few frames so that the visual indication is not visible, is barely visible, and/or quickly disappears. When there is persistence, the frame-by-frame rotational motion may be visible and detectable to a viewer.

Figure 2:
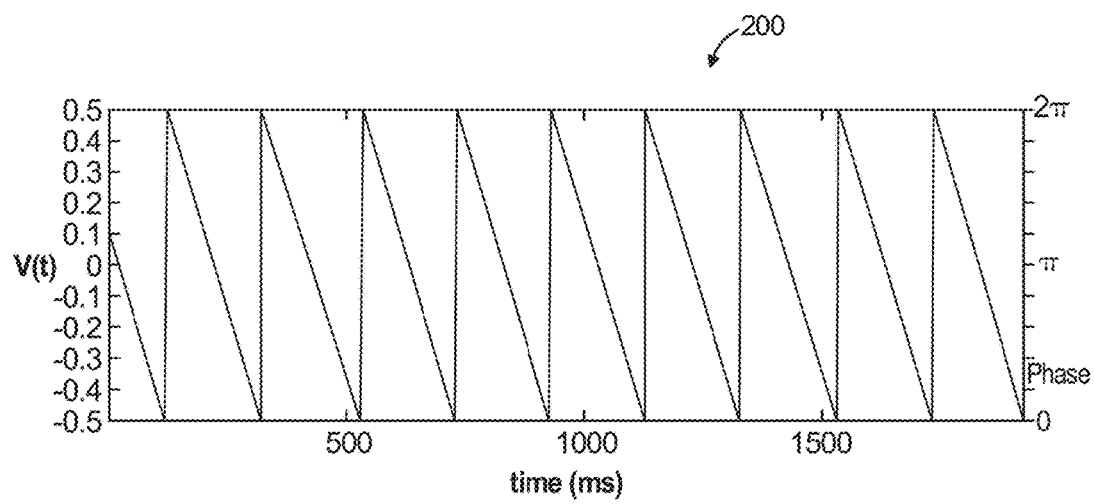
FIG. 2 illustrates an example phase-time curve related to electrical signals sensed by a sensor positioned in relation to a heart illustrated in FIG. 1.
Figure 3:
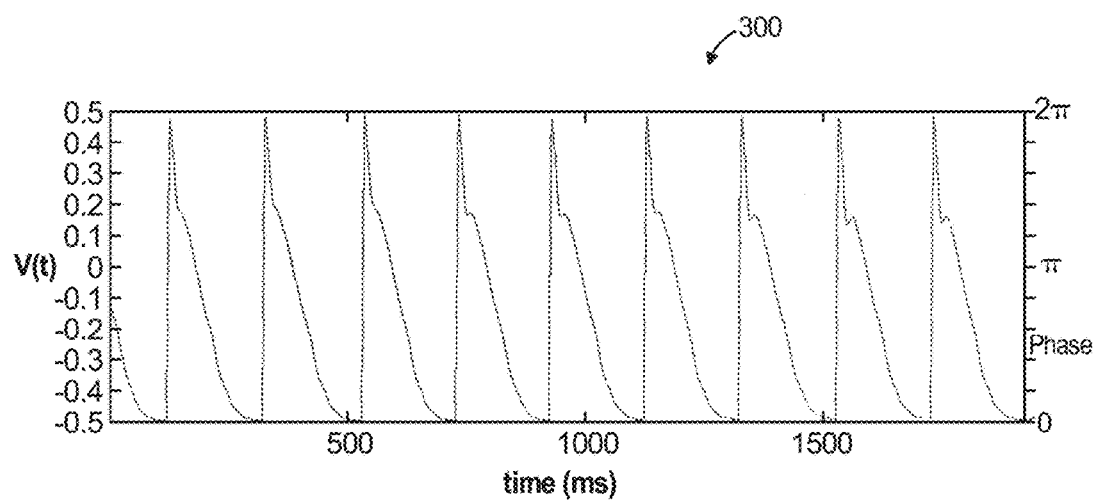
FIG. 3 illustrates another example phase-time curve related to electrical signals sensed by a sensor positioned in relation to the heart illustrated in FIG. 1.

FIG. 2 illustrates a phase-time curve 200 generated from voltage-time data of MAP signals obtained during the heart rhythm disorder, for one preferred embodiment of rotational driver detection via phase mapping. The phase-time data and phase time curve 200 are generated by processing MAP signals, including converting the voltage-time data represented by MAPs into the phase-time data with noise-reduction and further processing of the data. The voltage-time to phase-time data conversions used for generating curve 200 may be performed by multiplying a normalized voltage of sampled data points along the MAP signal (which may be approximated) by 2π. The phase-time data is plotted on x-y axes corresponding to time and phase, respectively. Voltage-time to phase-time data conversions are understood by a person having skill in the art. The representation used in the present example is a sawtooth approximation. The approximation may be performed on the MAP signal before the conversion or after the conversion. The phase-time data shown in FIG. 2 approximates the MAP signal (that actually has four distinct phases, as shown in FIG. 3, but approximates a triangle) with a straight line. A portion of a MAP representation curve signal extending between a detected activation onset and a detected beginning of repolarization is approximated with a straight line. Similarly, a portion of the MAP signal extending from the beginning of repolarization to a next activation onset time is approximated with a straight line. Either or both approximations may be used.

FIG. 3 shows an example phase-time curve 300 that is also converted from voltage-time data associated with MAP signals and then converted to phase-time data, as described above. As shown, an approximation is not used to generate the phase-time data represented by phase-time curve 300.

The computing device 116 generates, accesses, or receives phase-time data, phase-time curves 200, 300 and/or the APM 150. The APM 150 spatially arranges MAPs on a display that may be a two-dimensional or three-dimensional display, such as a model shaped as the heart 120. The spatial arrangement is relative to the physical sensor locations 104 in relation to the heart 120. Similarly, other systems and methods that can reconstruct cardiac or biological electrical information to provide representations of cardiac electrical activity having activation onset information may be used to generate the APM 150.

Figure 4:
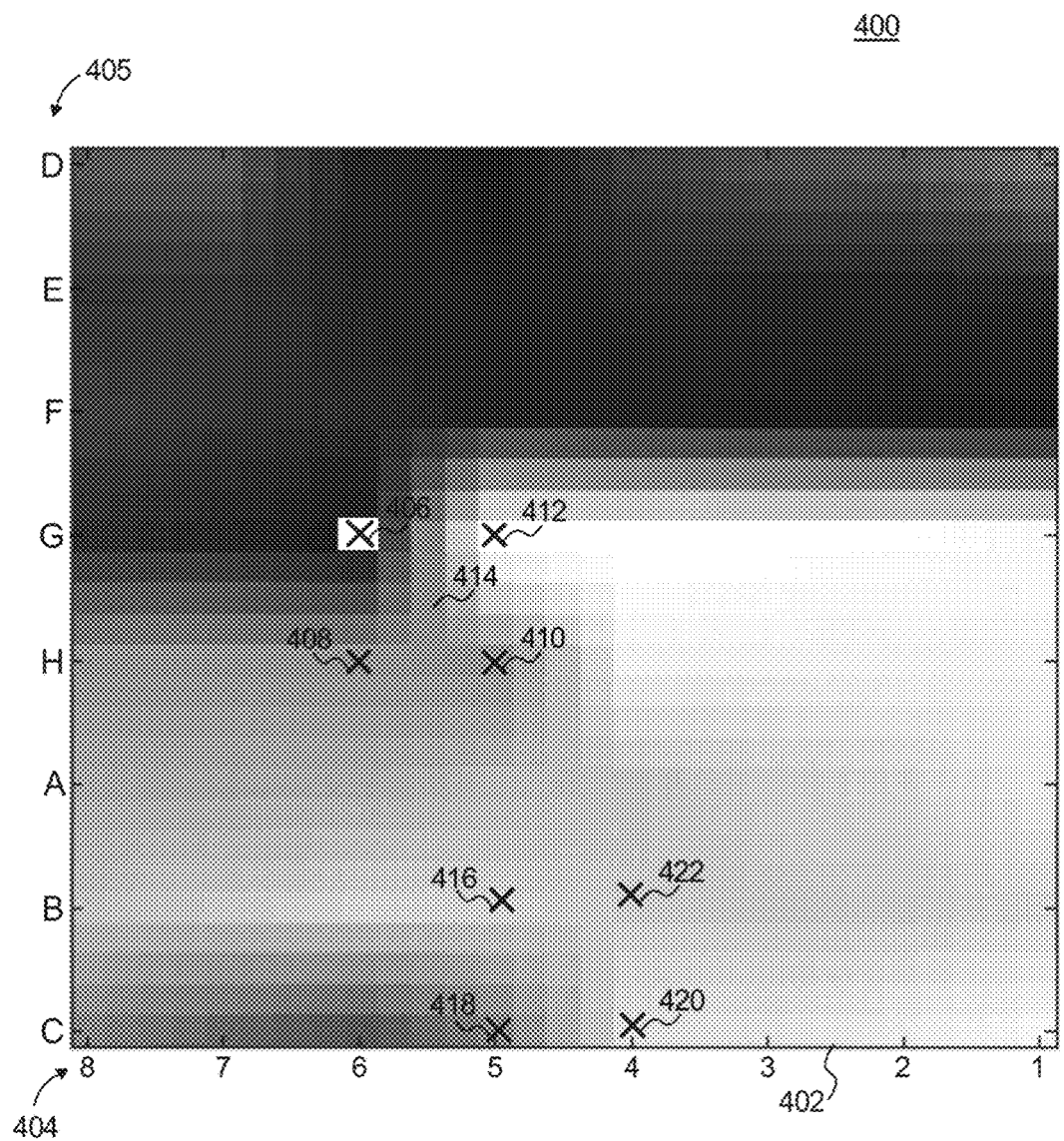
FIG. 4 illustrates a grid with sensing elements related to locations of sensors illustrated in FIG. 1.

FIG. 4 provides an example two-dimensional APM frame 400 of a series of frames (e.g., an APM video 150) that correspond to sequential, evenly-spaced time increments (e.g., every millisecond (msec) or every 10 msec) in a time interval. The time interval can be two-ten seconds, or a different interval. Each APM frame 400 can be generated by sampling multiple MAP signals at time t of the time interval.

APM frame 400 includes a grid 402 having an electrode reference 404 labeled 1-8 and a spline reference 405 labeled A-H. The electrode reference 404 and spline reference 405 have 64 intersecting elements, also referred to as sensor elements, which correspond to respective sensors 104 of the array of sensors (e.g., 64 sensors). Four example sensor elements 406, 408, 410, 412 correspond to respective intersections on the grid 402 (1-8, A-H), and further correspond to respective sensors 104 of the array of sensors. Specifically, the sensor elements 406, 408, 410, 412 are located on grid 402 at intersecting elements that may be labeled (6,G), (6,H), (5,H), and (5,G), respectively.

Grid 402 is segmented into a plurality of areas, with each area defined or bounded by at least three sensor elements. The areas are configured as polygons (e.g., a triangle, rectangle, or square), and some cases can cover the entire grid 402. The sensor elements that define each area are positioned at vertices of the area. An example area 414 is a square having vertices at intersecting elements that may be labeled (6,G), (6,H), (5,H), and (5,G). Area 414 is defined by sensor elements 406, 408, 410, 412 that are positioned at the four vertices of a square (G-H, 6-5). In the example shown, the entire grid 402 is covered by contiguous, non-overlapping square areas, with each square area being bounded or defined by four sensor elements. Area 414 corresponds to an area of the heart 120 defined or bounded by the sensors 104, which correspond to the sensor elements 406, 408, 410, 412. In another embodiment, the areas may overlap. Similarly, an example second area is defined by sensor elements 416, 418, 420, 422, which correspond to respective sensors 104.

The sensor elements of the APM frame 400 are assigned a gray-scale level that corresponds to the voltage (or charge) of the MAP signals. The gray-scale levels for elements located between the sensor elements 406, 408, 410, 412 may be determined using interpolation (e.g., based on the representative MAP signals). The '666 patent and U.S. Pat. No. 8,700,140, which are incorporated herein by reference in their entirety, describe systems and methods to generate a series of APM frames.

A series of APM frames 400 may be displayed in a sequence, e.g., as a video stream (APM video 150). A viewer may be able to see changes in the represented voltage (or charge) depicted over time. This approach may display either a rotational or focal driver. In this example, the change in voltage has a rotational pattern over time, indicating that a phase singularity has been sensed by sensors 104. Notably, the displayed rotational patterns may not be indicative of a phase singularity that is associated with a cardiac rhythm disorder. Rotational patterns less likely to indicate drivers of heart rhythm disorders are inconsistent, fleeting, and/or non-persistent; they may change rotational direction and/or have an insubstantial degree of rotation. In fact, some of the rotational patterns may not be displayed for a sufficient number of frames to be visible to a viewer, whereas other rotational patterns may be visible, but may then disappear. Despite all of this, the APM video 150 of APM frames 400 can provide useful information to a surgeon, including dynamic changes over time and the rotational patterns on the grid 402.

In one aspect, the present disclosure provides a system and method that sums, for all of the time increments in a time interval, rotational activity associated with each area on the grid 402. The total sum is indicative of a phase singularity located at that area. Excluded from the sum, however, is rotational activity that occurs in opposite directions at the same area and rotational activity that has an insubstantial degree of rotation (e.g., satisfies criteria in accordance with the disclosed method described below). The sum is recorded by a rotational counter associated with each area of the grid 402. The rotational counter is modified, e.g., incremented, each time there is rotational activity having a substantial degree of rotation in the associated area. When the time interval is ended, the magnitude of the rotational counter associated with each area of the grid 402 indicates the existence and degree of persistence of phase singularities at each area of the grid 402.

Figure 5:
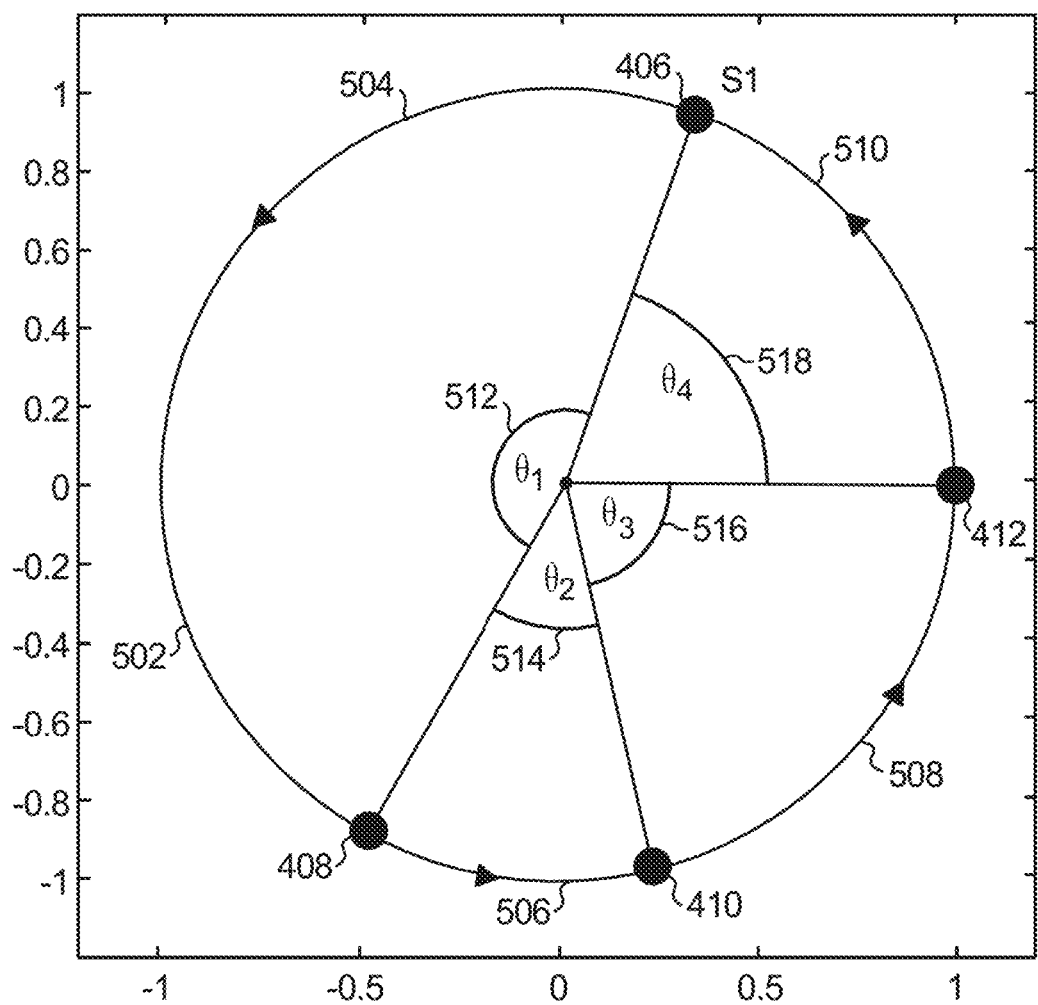
FIG. 5 illustrates a first example unit circle showing sensor elements illustrated in FIG. 4 with a first set of phase values.
Figure 6:
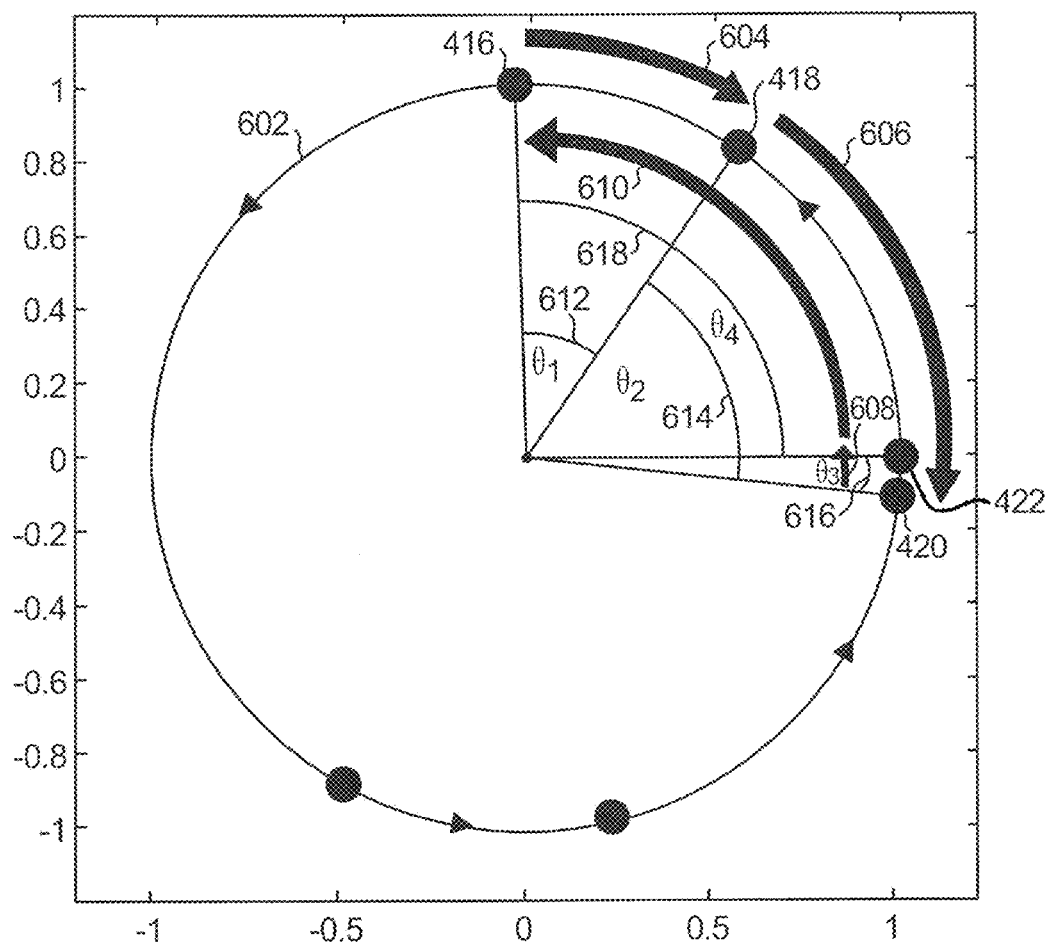
FIG. 6 illustrates a second example unit circle showing the sensor elements illustrated in FIG. 4 with a second set of different phase values.

Turning now to FIGS. 5 and 6, a method is described for determining whether rotational activity at time t has a substantial degree of rotation that would warrant incrementing the rotational counter. For each time t, a phase sum is calculated for each area on grid 402. The phase sum is calculated by determining a shortest path between a sequence of the sensor elements (406, 408, 410, 412) beginning and ending at a first sensor element of the sequence, calculating a phase difference between the sensor elements in the sequence using a shortest path, and summing the phase differences. The calculated phase sum result may be 0, 2π, or −2π. Phase sum=0 indicates insufficient rotational activity for incrementing the rotational counter and indicates that no net rotation is present. Phase sum=2π or −2π indicates that the rotational counter should be updated, e.g., incremented or decremented, respectively, and indicates that rotation occurs, with the positive or negative sign indicative of a clockwise or counterclockwise direction of rotation (e.g., depending on a convention selected).

FIG. 5 illustrates an example method for calculating phase sum at time t for the area 414 defined by sensor elements 406, 408, 410, and 412 in FIG. 4. A unit circle 502 having radius=1 is provided. Sensor elements 406, 408, 410, and 412 are disposed on the circumference of the unit circle 502 in accordance with a phase associated with each of the respective sensor elements 406, 408, 410, and 412. The phase associated with each sensor element 406, 408, 410, and 412 is determined from the phase at time t along the corresponding phase-time curve, e.g., phase-time curves 200 or 300.

Any sensor element may be selected to be the first sensor element. The sensor elements are then processed in a selected sequence. The sequence may be based on the position of sensor elements 406, 408, 410, and 412 on grid 402, by proceeding in a counterclockwise or clockwise direction around area 414 among the sensor elements in accordance with their arrangement on grid 402, beginning with the first selected sensor element and ending with the first sensor element. In this example, sensor elements are ordered as 406, 408, 410, 412. As shown, sensor element 406 is selected to be the first sensor element.

The shortest path is determined between the first sensor element 406 and the second sensor element 408. The path 504 in the counterclockwise direction is shorter than an alternative path in the clockwise direction. Therefore, path 504 is determined to be the shortest path between first and second sensor elements 406 and 408.

The phase difference 512 between the sensor elements 406 and 408 for shortest path 504 is determined. In the example shown in FIG. 5, the selected convention sets a negative value for a clockwise direction and a positive value for a counterclockwise direction. Thus, the phase difference 512 is assigned a positive value because it moves in a counterclockwise direction along the shortest path 504 from sensor element 406 to sensor element 408. Note that the convention is reversible to otherwise set a positive value for a clockwise direction and negative value for a counterclockwise direction.

The shortest path and phase difference are similarly determined for each of the sensor element pairs 408 and 410, 410 and 412, and further, 412 and the first sensor element 406. The shortest paths, respectively, are 506, 508, and 510, all being in the counterclockwise direction. Thus, the respective phase differences 514, 516, and 518 are all positive. The four phase differences 512-518 are summed to determine the phase sum. Since the entire circumference of the unit circle is traversed in the counterclockwise direction along the shortest paths 504-510, all of the phase differences are positive. The phase sum=2π, indicating the possible presence of a rotational driver.

The example in FIG. 5 illustrates that there is an indication of a rotational driver when a full circle around the unit circle 502 is completed by following the shortest paths between sensor elements 406, 408, 410, 412 disposed on the unit circle 502, including back to the first sensor element 406. When the rotation between the sensors 104 is in one direction, the phase differences are all positive or all negative and do not cancel each other out. This results in a phase sum=2π, which indicates that the rotational activity measured at the corresponding sensors 104 is consistent with a rotational driver of the heart rhythm disorder.

FIG. 6 illustrates another example for calculating phase sum at time t for another area of the grid 402. A unit circle 602 having radius=1 is provided with sensor elements 416, 418, 420, and 422 disposed on the circumference of unit circle 602.

The shortest path 604 is determined between the first sensor element 416 and the second sensor element 418. The path 604 in the clockwise direction is shorter than an alternative path in the counterclockwise direction. Therefore, the shortest path here is determined to be the shortest path 604 (based on the selected convention of a negative value for a clockwise direction).

The phase difference 612 between the sensor elements 416 and 418 for the shortest path 604 is determined. The phase difference 612 is assigned a negative value because the shortest path 604 from sensor element 416 to sensor element 418 traverses the circumference of the unit circle 602 in a clockwise direction, (based on the selected convention of a negative value for a clockwise direction).

The shortest path and phase difference are similarly determined for each of sensor element pairs 418 and 420, 420 and 422, and 422 and the first sensor element 416. The shortest paths, respectively, are 606, 608, and 610. Shortest path 606 is directed in a clockwise direction. Therefore, phase difference 614 has a negative value. Shortest paths 608 and 610 are in a counterclockwise direction. Therefore, phase differences 616 and 618 have positive values. The phase differences 612 and 614 cancel out the phase differences 616 and 618, since they are equal in magnitude when summed, but opposite in direction. Thus, the sum of phase differences 612-618 is zero (0), which indicates the absence of a phase singularity at this area.

The example in FIG. 6 illustrates that there is no indication of rotation when a full circle around the unit circle 602 cannot be completed by following the shortest paths between sensor elements 416, 418, 420, 422 disposed on the unit circle 602, including back to the first sensor element 416. When the rotation between the sensors 104 is in different directions (clockwise and counterclockwise), then some phase differences are positive and some are negative, thereby cancelling each other out. This results in a phase sum=0, which indicates that the rotational activity measured at the corresponding sensors 104 is insufficient to indicate a rotational driver.

Figure 7:
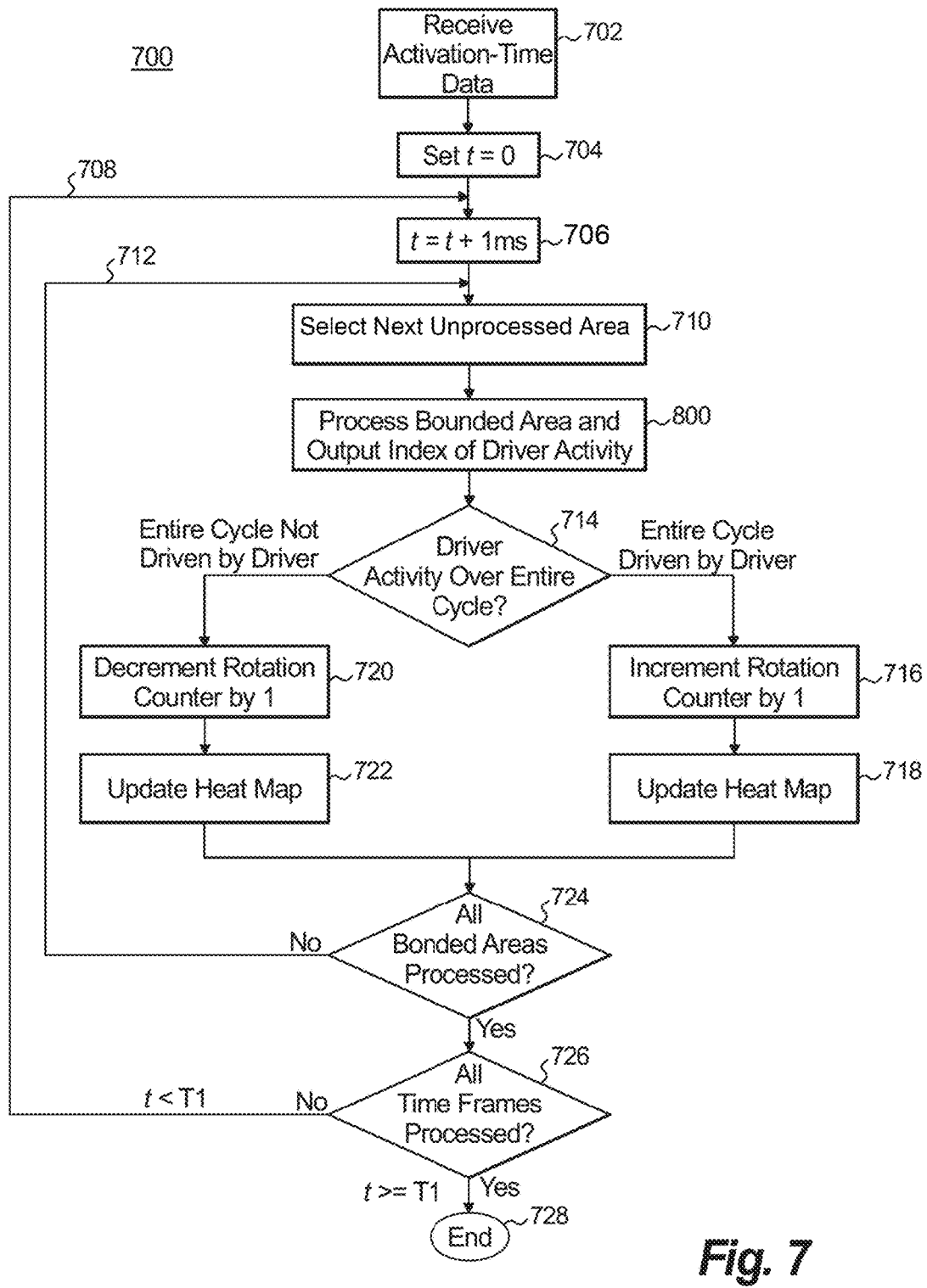
FIG. 7 illustrates a flowchart that shows an example method for summing (counting) indexes of rotational activity or centrifugal activation associated with a localized driver associated with areas of the grid illustrated in FIG. 4 over a time interval.
Figure 8:
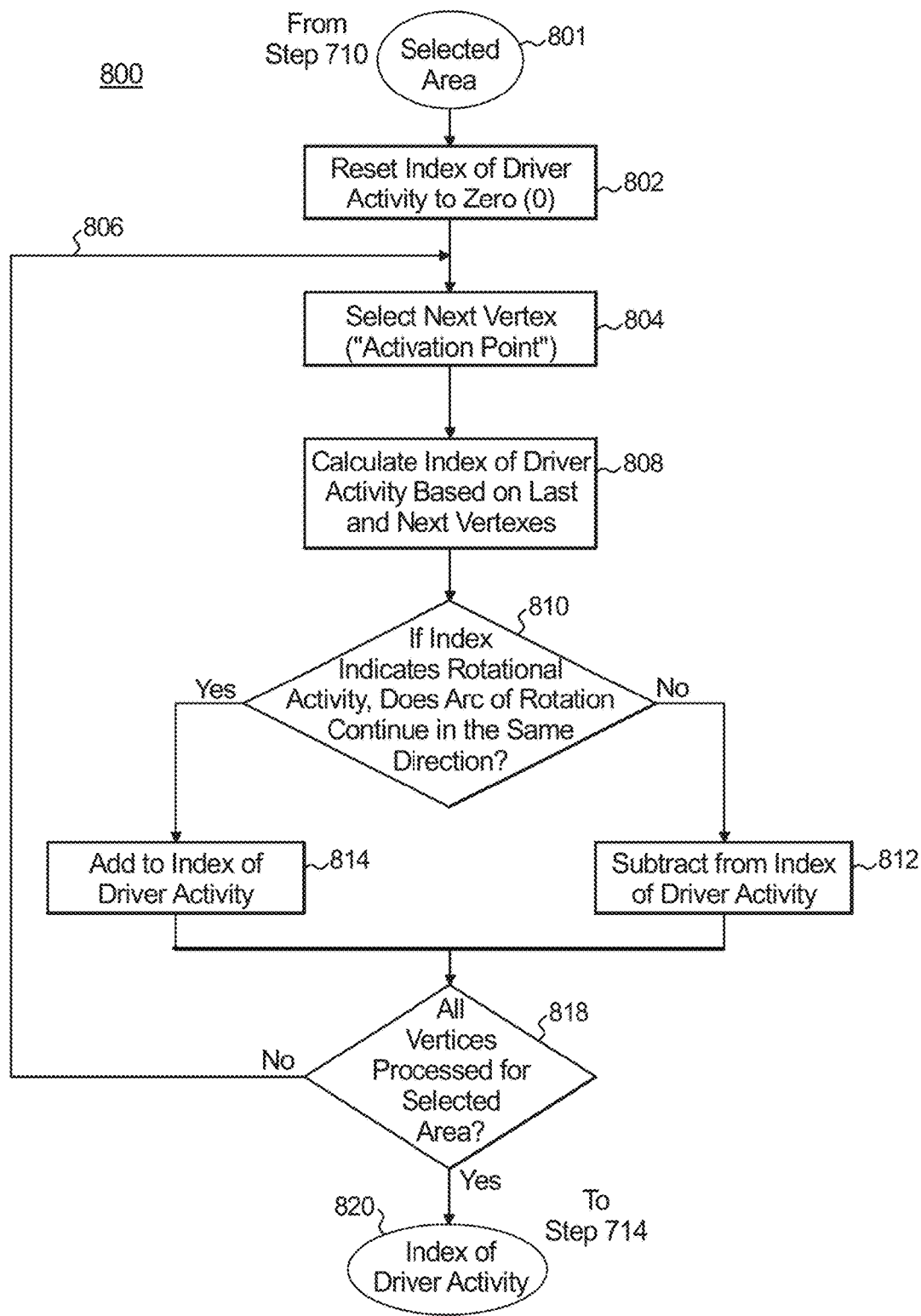
FIG. 8 illustrates a flowchart that shows an example method for summing an index of driver activity within an area of the grid illustrated in FIG. 7.

FIGS. 7-8 provide example flow diagrams that describe an example method 700 to process activation-time data for a time interval TI in order to detect rotational activation that is sufficiently significant and persistent to indicate the existence of a source of a cardiac rhythm disorder.

Importantly, the flowcharts outline a method and a system to sum indexes of rotational activation (detected for instance, via singularities or angles of rotation) as well as focal drivers (detected, for instance, from centrifugal activation). This is important since both may coexist, and because the principle of centrifugal activation from a source may apply whether the driver associated with the source is focal or rotational. Thus, all analyses included in this specification include either analyses (summation) of indexes of rotational activation, indexes of centrifugal activation (that may be centripetal if the source moves) or a combination over time.

The method further includes generating a visual quantitative display of the persistence of drivers of sources associated with heart rhythm disorders. The heat map indicates locations in grid 402 associated with persistent rotations and/or the degree of the persistence. Heat map displays the areas of grid 402 and assigns each area a visual indication (e.g., color, shade, or intensity) that indicates the magnitude of the rotational counter associated with that area. When the rotational counter associated with an area is incremented or decremented by 1, the visual indication associated with that area is increased or decreased, respectively, by one unit to show the change in the rotational counter. A unit of a visual indication may be for example, a spectral unit, e.g., along the rainbow spectrum, such as wherein red is at the high end and violet is at the low end, a shade of gray unit, or an intensity unit. These units can be dimensionless, can indicate a ratio relative to a baseline uniform (non-rotational) propagation field, or can have other dimensions. This will vary with the specific heart rhythm disorder and signal source under consideration, but may include degrees (radians) or persistent rotation, a ratio (%) of persistence across a number of cycles, a correlation value (dimensionless) and other dimensions.

The heat map may include a single map or a video including a series of maps. The heat map may be displayed independently or overlaid (e.g., superimposed) over another map, such as an APM frame or a structural map of a corresponding biological structure, e.g., the heart 120. When the heat map is overlaid over an APM frame, such as being overlaid over an APM video 150, they are synchronized to display information relating to the same time increment. Additionally, they are spatially consistent with one another in reference to the biological structure (e.g., heart 120).

At step 702, activation-time data is accessed or received. The activation-time data may be accessed in real time during a procedure in which sensors 104 generate sensing data, or after a procedure is completed. The activation-time data may be accessed from a computing device 116 or a remote device, such as via wired or wireless communication.

At initialization step 704, a time counter, t, is initialized by setting t=0. Also, the rotational counter associated with each area of grid 402 is initialized by setting each rotational counter=0. Additionally, the heat map is initialized by setting the visual indication of each area of grid 402 to a neutral visual indication that indicates rotational counter=0 for that area.

At step 706, an outer loop 708 commences to iteratively process all time increments within time interval TI. Step 706 increments t by a predetermined time increment which, in the current example, is one (1) msec. At step 710, an inner loop 712 commences to iteratively process each area included in grid 402 (shown in FIG. 4). Accordingly, loops 708 and 712 process all areas of grid 402 for each incremental time t.

At step 710, a next unprocessed area of grid 402 is selected. For the first pass through the inner loop 712, a first area is selected. For example, the first area may be selected to be the square area bounded by sensor elements 104, with the first area being located in the upper left hand corner of grid 402 at grid intersections (8, D), (8, E), (7, E), and (7, D). The second selected area may also be adjacent to the previously selected area 414. Accordingly, in the example shown, inner loop 712 is processed forty-nine (49) times until each of the forty-nine (49) areas provided in grid 402 is processed for the current time t. The order of processing the forty-nine (49) areas may be predefined, but is not limited to any particular order.

The selected area 414 is processed at step 800 to calculate an index of driver activity for the selected area 414. Accordingly, the grid intersections for sensor elements 406-412 that define the selected area 414 are provided as input to step 800. The index of driver activity for the selected area 414 is determined at step 800. Step 800 outputs the index of driver activity for the selected area 414, after which control passes to determination step 714. Step 800 is described below in greater detail with respect to FIG. 8.

At step 714, a determination is made whether driver activity is over an entire cycle. If the entire cycle is driven by the driver, then control passes to step 716. If the entire cycle is not driven by the driver, then control passes to step 720.

At step 716, a rotational counter associated with the currently selected area is incremented by a count of one. At step 718, the heat map is updated by increasing the visual indication associated with the selected area by one unit. Then, control passes to step 724, the end of inner-loop 712.

At step 720, the rotational counter is decremented by a count of one. At step 722, the heat map is updated by decreasing the visual indication associated with the selected area by one unit. Then, control passes to step 724, the end of inner-loop 712.

At step 724, a determination is made whether all areas were processed for time=t. If not, execution passes to step 710, and another pass of inner-loop 712 is processed for the next area until all of the areas of grid 402 have been processed. If the determination at step 724 is that all areas have been processed for time=t, then execution proceeds to step 726, the end of outer-loop 708, to determine whether all frames for interval TI were processed (e.g., t>=TI).

If the determination at step 726 is that t<TI, meaning that there are more time frames (increments) to process for interval TI, then control returns to step 706 and a next pass of outer-loop 708 is performed for the next time increment. If the determination at step 726 is that t=TI, meaning that all of the frames in interval TI have been processed, then outer-loop 708 is terminated, and control passes to step 728, at which the method 700 ends.

In operation, during each iteration of outer-loop 708 at time t, all areas are processed and the rotational counter and the visual indication of the heat map associated with each area are updated and summed. Thus, with each subsequent iteration of outer-loop 708, the rotational counter associated with each area is updated by incrementing or decrementing the rotational counter, depending on the rotational direction. When a possible rotational driver having the same rotational direction is detected in an area in many iterations of outer-loop 708, the rotational counter associated with that area is successively incremented (or decremented, depending upon polarity) and achieves a relatively high magnitude in the positive or negative direction, indicating the presence of persistent rotational activation in a counterclockwise or clockwise direction at the area.

On the other hand, when opposite rotational directions occur during different iterations of outer-loop 708, the rotational counter is incremented and then decremented (or vice versa), cancelling out an increase in magnitude (herein referring to the rotational counter absolute value), indicating that a persistent rotational driver does not exist at the area. Accordingly, the magnitude of the rotational counter associated with each area is indicative of the persistence of rotation in a consistent rotational direction.

In some aspects, the heat map may include only the final frame, and/or the final magnitude of the rotational counter for each area may be reported. The magnitude of each rotational counter indicates whether rotation occurs in the associated area and its degree of persistence. The final magnitude of the rotational counter associated with the respective area may be compared to a predetermined threshold. If the rotational counter exceeds the threshold, a determination may be made that persistent rotation occurs in the associated area. While the final magnitude of the rotational counter provides static quantitative information, the final heat map frame provides static qualitative visual information about the existence and persistence of rotational patterns.

In other aspects in which the method 700 is performed, when the phase-time data for the entire time interval and/or all of the areas is available before beginning execution of step 704, some or all of the execution steps in the example method 700 may be performed in a different order, serially, in parallel, or a combination thereof, as opposed to iteratively. Steps associated with different frames and/or different areas may be performed in a different order, serially, in parallel, or a combination thereof. The method 700 ends at step 728.

With reference to FIG. 8, an example method is shown for executing step 800 in FIG. 7. The method processes an area and determines an index of driver activity for the area. -At input step 801 the identification of the area selected at step 710 in FIG. 7 is provided as input. The input includes identification of the sensor elements that define the selected area. In the present example, the selected area is area 414 which is defined by the sensor elements 406-412.

At step 802, the index of driver activity is initialized to 0. At step 804, a loop 806 commences for iteratively selecting, in a sequence, sensor elements 406-412 that define the area 414, for example. In the current example, sensor element 406 is selected for the first pass through loop 806. Sensor elements 408, 410, and 412 are selected sequentially for subsequent respective passes through loop 806. The example sequence describes a counterclockwise path around area 414. Other sequences may be selected.

At step 808, the index of driver activity is determined based on last and next vertexes of a selected area, e.g., between a selected sensor element and the next sensor element in the sequence, moving from the selected sensor element to the next sensor element in a selected direction (e.g., clockwise or counterclockwise). It is noted that the same selected direction is used for all iterations of loop 806. In the present example, during the first pass through loop 806, the index of driver activity between sensor elements 406 and 408 is determined. During the second, third and fourth passes, respectively, the index of driver activity between sensor elements is determined. At step 810, a determination is made as to whether an arc of rotation continues in the same direction. If "No", step 812 is executed to adjust the index of driver activity, e.g., subtracting a value from the index of the driver activity. If "Yes", step 814 is executed to adjust the index of driver activity, e.g., adding a value to the index of the driver activity.

At step 818 (the end of loop 806), a determination is made whether all vertexes (e.g., sensor elements 406-412) were processed for the selected area 414. If not, control returns to step 804 to select the next sensor element in the sequence and to execute loop 806 with the newly selected sensor element. After the final iteration of loop 806, at step 818 a determination is made whether all of the sensor elements have been selected and processed. If so, the index of driver activity is output at step 820, and control passes to step 714 of FIG. 7.

Now with reference to FIG. 7, the heat map generated by the computing device 116 is overlaid on an APM frame 400. The heat map may include a series of frames that correspond to the time increments associated with each iteration of outer-loop 708. The heat map uses a visual indication, such as color, intensity, or shades of gray to indicate the magnitude of the rotational counter associated with each area of grid 402. The higher the magnitude of the rotational counter, the stronger the persistence of detected rotational activation areas.

Different colors or shades of gray may be assigned to various rotational counter magnitudes. The colors and shades of the heat map may be translucent so that when overlaid over another map, graphic, text, or the like, the underlying information may be visible. In a multicolor configuration, for example, warm colors may be assigned to the higher rotational counter magnitudes, and cool colors may be assigned to the lower rotational counter magnitudes (e.g., based on the rainbow spectrum), with red indicating the highest magnitude and purple representing the lowest. In a gray-scale configuration, for example, light shades may be assigned to the higher magnitudes and dark shades may be assigned to the lower magnitudes, with white indicating the highest magnitude, and black representing the lowest magnitude.

In the current example, a single color, e.g., red, is used, and the intensity of the color increases with the magnitude of the rotational counter. When the rotational counter=0, the color is not displayed.

As iterations of outer-loop 708 are processed and the rotational counter is updated, the heat map is updated frame by frame. Thus, each frame of heat map represents a summation of the previous frames. Throughout the summation, an increase of magnitude of the rotational counter indicates existence of and persistence of a detected rotational pattern. When step 728 is reached, a final frame of the heat map has been generated and the heat map is complete. The final frame shows the summation of all the previous frames and graphically shows persistent rotations, their location on the grid 402, and the degree of their persistence.

The displayed heat map indicates the location of a persistent rotational pattern (driver) to a viewer, e.g., a surgeon. The surgeon may use that information to identify a source associated with a cardiac rhythm disorder. Accordingly, the surgeon may treat cardiac tissue at the source, and/or the rotational pattern (driver) that drives the source, or within a possible margin of tissue to suppress or eliminate the cardiac rhythm disorder.

The series of frames of the heat map may be stored and replayed. Since the information is summed for all areas of grid 402 with each iteration of outer-loop 708, as the series of frames of the heat map video is replayed, the visual indications of persistence are dynamic, with persistent electrical rotation shown increasing in intensity, and fleeting electrical rotation or noise either not visible, or visible for a short duration and then disappearing or fading.

The grid 402 may be normalized with respect to a preference value. The preference value may be used to set a most significant value to one (1), with the others assuming a range between zero (0) and one (1). Alternatively, the grid 402 may be normalized with respect to the time analyzed, reflecting a percentage of time during which detected phase singularities are present.

Figure 9:
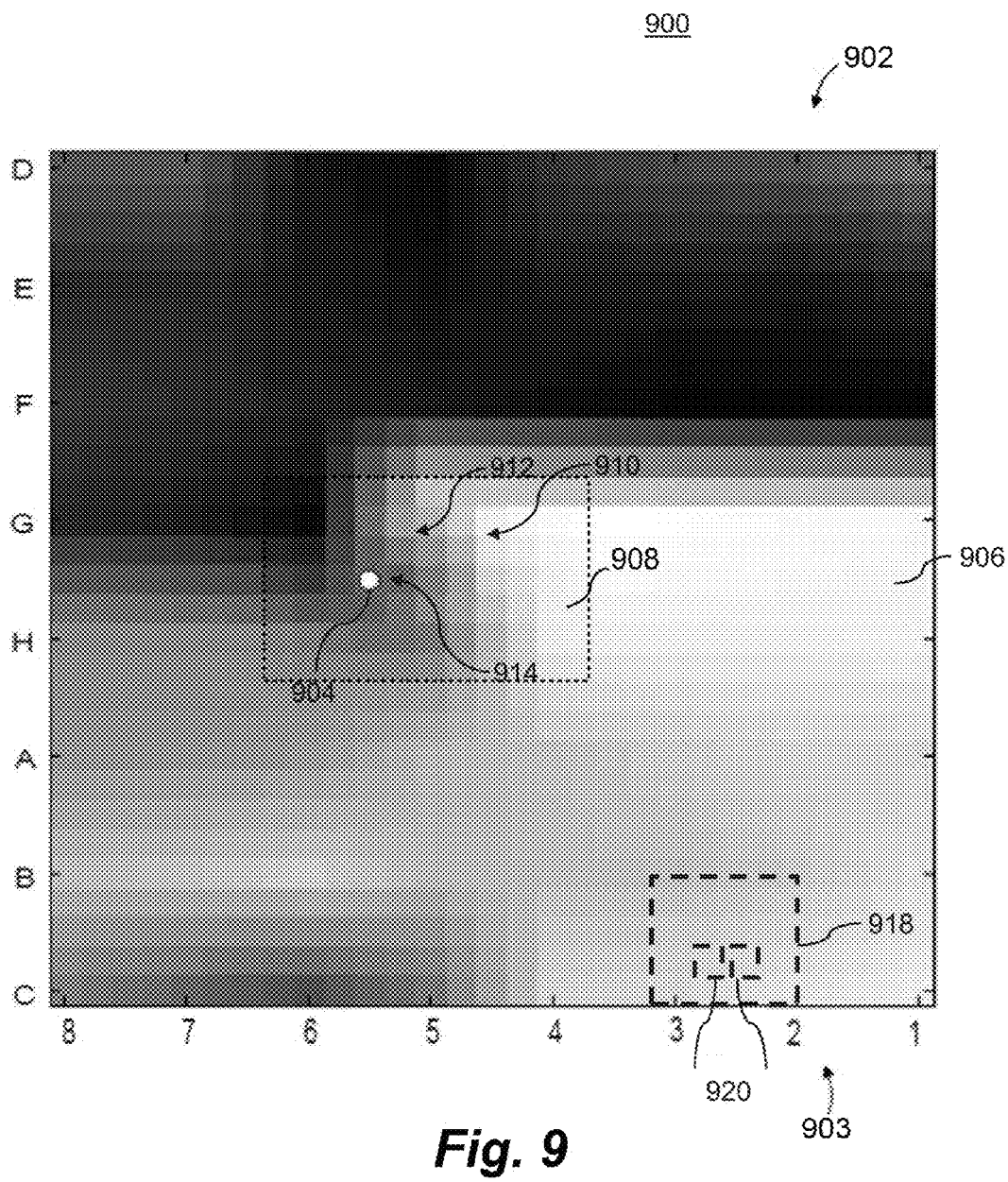
FIG. 9 illustrates a heat map, which indicates the persistence of a rotational driver (illustrated) or focal driver associated with a source of the heart rhythm disorder, and which is superimposed on an activation propagation map.

FIG. 9 shows a frame 900 that includes a heat map frame 902 overlaid over an APM frame 903. APM frame 903 may be a single stand-alone frame or may belong to a series of APM frames, e.g., a video 150. When the heat map 902 video is overlaid over an APM video, the maps can be synchronized so that the frames 902 and 903 correspond to the same time increment. Alternatively, they may be unsynchronized.

The example APM 903 includes an area of electrical activity 906 that moves about a central point, as seen when playing back previous frames. Based on information gathered in a single frame, the central point has been identified as a region having repeating activation indicated by a white dot 904. The heat map 902 includes an area 908 (indicated in red in the color drawing/surrounded by the dotted rectangle) that includes areas 910, 912, 914 of varying intensity, listed here from least to most intense. The red area 908 indicates that the rotational counter associated with that portion of heat map 902 has been incremented, with the intensity of the red area 908 increasing in areas 912 and 914 in accordance with the magnitude of the rotational counter. The most intense area 914 corresponds to the highest calculated magnitude of the rotational counter. The highest calculated magnitude of the rotational counter and the most intense area 914 may indicate the center (driver) of the electrical rotational activity 906, and be indicative of the source of a cardiac rhythm disorder. Here, the most intense area 914 is located near white dot 904 of the APM 903. Accordingly, the white dot 904 of the APM 903 is consistent with the intense red area 914 of the heat map 902.

An example area 918 is shown on heat map 902, with its boundaries indicated by dotted lines. The area 918 may include smaller elements 920. The visual indication associated with the area 918 may vary within the area 918, with different elements 920 appearing to have a different visual indication. Methods and calculations, such as interpolation, may be used to vary the visual indication of different elements 920 within area 918. Additionally, the appearance of the visual indication of the two elements 920 having the same visual indication may differ due to the underlying image, e.g., the APM 903.

The heat map 902 provides a summation of information that builds over the course of the video to display persistent patterns, and filters out events that do not have a significant amount of associated rotation. The combination of information provides the viewer with a combination of robust information, dynamic information and locational information.

Additionally or alternatively, the heat map 902 may be overlaid or superimposed on an image of the sensor locations and/or the anatomy where the sensors 104 are positioned. This combination of images may provide additional locational information relating the location of the persistent phase singularities relative to the location of the sensors 104.

Figure 10:
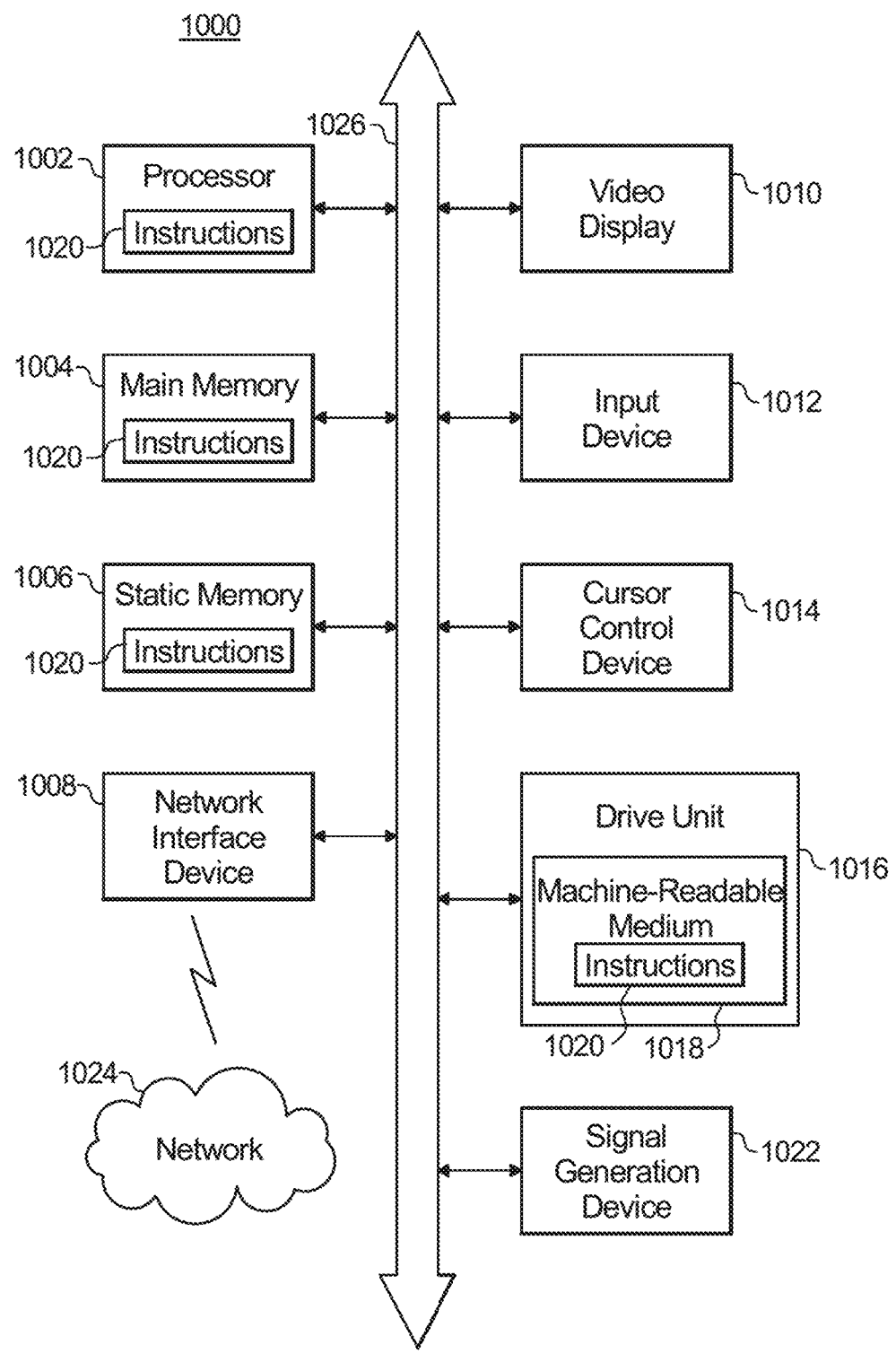
FIG. 10 illustrates a block diagram of an illustrative embodiment of a general computer system.

FIG. 10 is a block diagram of an illustrative embodiment of a general computing system 1000. The computing system 1000 can include a set of instructions that can be executed to cause the computing system 1000 to perform any one or more of the methods or computer based functions disclosed herein. The computing system 1000, or any portion thereof, may operate as a standalone device or may be connected, e.g., using a network 1024 or other connection, to other computing systems or peripheral devices.

The computing system 1000 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computing system 1000 is illustrated, the term "system" shall also be taken to include any collection of systems or sub-systems that individually or jointly execute a set, or multiple sets, of instructions to perform one or more computer functions.

As illustrated in FIG. 10, the computing system 1000 may include a processor 1002, e.g., a central processing unit (CPU), a graphics-processing unit (GPU), or both. Moreover, the computing system 1000 may include a main memory 1004 and a static memory 1006 that can communicate with each other via a bus 1026. As shown, the computing system 1000 may further include a video display unit 1010, such as a liquid crystal display (LCD), an organic light emitting diode (OLED), a flat panel display, a solid state display, or a cathode ray tube (CRT). Additionally, the computing system 1000 may include an input device 1012, such as a keyboard, and a cursor control device 1014, such as a mouse. The computing system 1000 can also include a disk drive unit 1016, a signal generation device 1022, such as a speaker or remote control, and a network interface device 1008.

In a particular embodiment or aspect, as depicted in FIG. 10, the disk drive unit 1016 may include a machine-readable or computer-readable medium 1018 in which one or more sets of instructions 1020, e.g., software, can be embedded, encoded or stored. Further, the instructions 1020 may embody one or more of the methods or logic as described herein. In a particular embodiment or aspect, the instructions 1020 may reside completely, or at least partially, within the main memory 1004, the static memory 1006, and/or within the processor 1002 during execution by the computing system 1000. The main memory 1004 and the processor 1002 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computing systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computing system processing can be constructed to implement one or more of the methods or functionality as described herein.

It is also contemplated that a computer-readable medium includes instructions 1020 or receives and executes instructions 1020 responsive to a propagated signal, so that a device connected to a network 1024 can communicate voice, video or data over the network 1024. Further, the instructions 1020 may be transmitted or received over the network 1024 via the network interface device 1008.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any tangible medium that is capable of storing or encoding a set of instructions for execution by a processor or that cause a computing system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture and store carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories A stored digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to define a rational source associated with a biological rhythm disorder, such a heart rhythm disorder, has been described herein. Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A method of identifying a region associated with controlling a source of a heart rhythm disorder, the method comprising:
   accessing, by a computing device, data from a plurality of sensors representing biological activity in the heart;
   identifying, by the computing device, a first and a second region of the heart comprising the source of the heart rhythm disorder, wherein the first region of the heart has repeating centrifugal activation; and
   determining, by the computing device, whether the first region controls the second region of the heart for at least a predetermined number of beats; and
   identifying the first region as controlling the source when the first region controls the second region for at least a predetermined number of beats.

2. The method of claim 1, wherein a sequence of centrifugal activation within the first region directly controls the second region.

3. The method of claim 1, wherein a sequence of centrifugal activation within the first region directly controls the second region in a centrifugal pattern.

4. The method of claim 1, wherein a sequence of centrifugal activation is spatially located within the first region between the beats.

5. The method of claim 1, wherein a sequence of centrifugal activation spatially moves within the first region between the beats.

6. The method of claim 1, wherein the first region has an area of less than 5 cm$^2$.

7. The method of claim 1, further comprising determining stability of the repeating activation by computing indexes of centrifugal activation within the first region.

8. The method of claim 7, wherein the indexes of centrifugal activation is one or more of vectors of activation, linear velocity, correlation analysis or and spatial maps showing progressive spatial activation.

9. The method of claim 7, wherein the indexes of centrifugal activation are displayed on a map of sensor locations indicating higher and lower indexes of centrifugal activation.

10. The method of claim 1, further comprising classifying the first region as a driver if the first region controls the second region for a plurality of the beats.

11. The method of claim 1, wherein the first region is a driver of the source.

12. The method of claim 11, wherein the driver is an internal driver of the source.

13. The method of claim 1, wherein the first region controls the source.

14. The method of claim 1, wherein the source is a focal source.

15. The method of claim 14, wherein the first region is a core of the focal source.

16. The method of claim 11, wherein the source comprises a focal source and the driver is a core of the focal source.

17. A system of identifying a region associated with controlling a source of a heart rhythm disorder, the system comprising:
 a processor; and
  a storage medium storing instructions that, when executed by the processor, cause the processor to perform operations comprising:
   accessing data from a plurality of sensors representing biological activity in the heart;
   identifying a first and a second region of the heart comprising the source of the heart rhythm disorder, wherein the first region has repeating centrifugal activation;
   determining whether the first region controls the second region of the heart for at least a predetermined number of beats; and
   identifying the first region as controlling the source when the first region controls the second region for at least the predetermined number of beats.

18. The system of claim 17, wherein a sequence of centrifugal activation within the first region directly controls the second region.

19. The system of claim 17, wherein a sequence of centrifugal activation within the first region directly controls the second region in a centrifugal pattern.

20. The system of claim 17, wherein a sequence of activation is spatially located within the first region between the beats.

21. The system of claim 17, wherein a sequence of activation moves spatially within the first region between the beats.

22. The system of claim 17, wherein the first region has an area of less than 5 cm$^2$.

23. The system of claim 17, further comprising determining stability of the repeating activation by computing indexes of centrifugal activation within the first region.

24. The system of claim 23, wherein the indexes of centrifugal activation includes one or more of vectors of activation, linear velocity, correlation analysis and spatial maps showing progressive spatial activation.

25. The system of claim 24, wherein the indexes of centrifugal activation are displayed on a map of sensor locations indicating higher and lower indexes of centrifugal activation.

26. The system of claim 17, further comprising classifying the first region as a driver if the first region controls the second region for a plurality of the beats.

27. The system of claim 17, wherein the first region is a driver of the source.

28. The system of claim 27, wherein the driver is an internal driver of the source.

29. The system of claim 27, wherein the source comprises a focal source and the driver is a core of the focal source.

30. The system of claim 17, wherein the first region controls the source.

31. The system of claim 17, wherein the source is a focal source.

32. The system of claim 31, wherein the first region is a core of the focal source.

* * * * *